United States Patent
Miyake et al.

[11] Patent Number: 6,033,074
[45] Date of Patent: Mar. 7, 2000

[54] SUBJECTIVE EYE REFRACTIVE POWER MEASURING APPARATUS

[75] Inventors: Nobuyuki Miyake, Hiratsuki; Ken Tomioka, Yokohama, both of Japan

[73] Assignee: Nikon Corporation, Tokyo, Japan

[21] Appl. No.: 09/207,501

[22] Filed: Dec. 8, 1998

[30] Foreign Application Priority Data

Dec. 9, 1997 [JP] Japan ................................. 9-356074
Apr. 2, 1998 [JP] Japan ................................. 10-090400

[51] Int. Cl.⁷ ............................................ A61B 3/10
[52] U.S. Cl. ................................................. 351/212
[58] Field of Search ................................. 351/205, 206, 351/211, 212, 222, 223

[56] References Cited

U.S. PATENT DOCUMENTS

| | | |
|---|---|---|
| 4,676,004 | 6/1987 | Nakamura et al. . |
| 4,878,750 | 11/1989 | Sekiguchi . |
| 4,917,480 | 4/1990 | Kato et al. . |
| 5,309,186 | 5/1994 | Mizuno ................................. 351/212 |
| 5,691,800 | 11/1997 | Iki et al. . |

FOREIGN PATENT DOCUMENTS

| | | |
|---|---|---|
| 0 349 228 A1 | 1/1990 | European Pat. Off. . |
| 0 722 690 A1 | 7/1996 | European Pat. Off. . |
| 2-124133 | 5/1990 | Japan . |
| 3-32637 | 2/1991 | Japan . |

*Primary Examiner*—George Manuel
*Attorney, Agent, or Firm*—Oliff & Berridge, PLC

[57] ABSTRACT

The subjective eye refractive power measuring apparatus according to the present invention objectively measures the refractive power of an optical system to be tested. The subjective eye refractive power measuring apparatus comprises a measuring element that output a detection signal corresponding to the refractive power of the optical system to be tested, an arithmetic device that calculates a measured value related to the refractive power based upon an output signal from the measuring element, a determination device that determines whether or not specific conditions related to termination of a measuring operation are satisfied based upon, at least, either a measured value obtained by the arithmetic device or the length of measurement time required for measurement and a termination device that implements specific control for terminating a measuring operation when the judgement device has determined that specific conditions are satisfied.

14 Claims, 11 Drawing Sheets

SUBJECTIVE EYE REFRACTIVE POWER MEASURING APPARATUS

INCORPORATED BY REFERENCE

The disclosures of the following priority applications are herein incorporated by reference:

Japanese Patent Application No. 9-356074, filed Dec. 9, 1997; and Japanese Patent Application No. 10-90400, filed Apr. 2, 1998.

1. Field of the Invention

The present invention relates to a subjective eye refractive power measuring apparatus that objectively measures the refractive power of an optical system being tested, and in particular, it relates to a subjective eye refractive power measuring apparatus which is characterized by its method of determining when a measuring operation is to be terminated.

2. Related Art

Subjective eye refractive power measuring apparatuses that objectively measure the refractive power of an optical system to be tested (hereafter used to refer to all lenses or lens groups that transmit light, or eyes to be tested, and more specifically, to refer to spectacle lenses, contact lenses, intra-ocular lenses or the like) based upon the principal of retinoscopy are widely used in the prior art (the refractive power measured by a subjective eye refractive power measuring apparatus, i.e., the spherical power, the cylindrical power and the like, is referred to as "measured values" as necessary).

Such subjective eye refractive power measuring apparatuses are primarily divided into stationary subjective eye refractive power measuring apparatuses and hand-held subjective eye refractive power measuring apparatuses according to the states in which they are employed. The following is an explanation of examples of a stationary subjective eye refractive power measuring apparatus and a hand-held subjective eye refractive power measuring apparatus, employed to measure eyes to be tested among various optical systems to be tested.

FIG. 8 presents an external appearance of a stationary type subjective eye refractive power measuring apparatus viewed from the direction of a side surface, illustrated together with a subject. As illustrated in FIG. 8, the stationary subjective eye refractive power measuring apparatus is provided with a chin receptacle 70, and a forehead pad 71 which are used to secure the subject at the subjective eye refractive power measuring apparatus. Then the operator operates a joystick while observing the eye to be tested displayed on a monitor 72 and moves a sliding table 73 back and forth, left and right and up and down to find the position at which the optical axis of a measuring optical system provided inside a measuring device and the optical axis of the eye to be tested are aligned with each other to adjust the alignment state of the subjective eye refractive power measuring apparatus relative to the eye to be tested. When the correct alignment state is achieved, the operator presses a switch 74 to start the measurement.

FIG. 9 presents an external appearance of a hand-held subjective eye refractive power measuring apparatus viewed from the direction of a side surface, illustrated together with a subject. As shown in FIG. 9, the hand-held subjective eye refractive power measuring apparatus is not normally provided with a chin receptacle or a forehead pad and, as a result, the subject cannot be completely secured to the subjective eye refractive power measuring apparatus. The operator moves the entire apparatus back and forth, left and right, and up and down, to find the position at which the optical axis of a measuring optical system provided inside the apparatus and the optical axis of the eye to be tested are aligned with each other while observing the eye to be tested displayed on a monitor 75 to adjust the alignment state of the subjective eye refractive power measuring apparatus relative to the eye to be tested. The alignment state is monitored by the apparatus itself, and a measuring operation starts automatically when the correct alignment state is achieved. An example of such a hand-held subjective eye refractive power measuring apparatus is disclosed in Japanese Unexamined Patent Publication No. H3-32637.

With one measurement defined as a measuring process through which, after the measurement is started, one measured value is obtained, a plurality of measurements are performed continuously for one optical system to be tested such as an eye to be tested in stationary and hand-held subjective eye refractive power measuring apparatuses in the prior art. The reason for this is that the measured value obtained through one measurement may not always be accurate since the alignment state may become offset by an abrupt gross movement of the eye to be tested occurring during the measurement or the subject may become nervous or look at a nearby object to cause a visual acuity adjustment of the eye to be tested even though the measurement must be implemented in a state in which no visual acuity adjustment is occurring at the eye to be tested.

Thus, conventionally a plurality of measurements have to be performed and the operator has to confirm whether there are any inconsistency or fluctuation among the plurality of measured values obtained through the plurality of measurements. The measuring operation is terminated when the operator determines that the measured values obtained through the measurements are reliable by verifying that there is only a small degree of inconsistency or fluctuation.

In addition, subjective eye refractive power measuring apparatuses that automatically calculate and display a reliability factor for measured values have been proposed in recent years to facilitate decision-making to be performed by the operator as described above in regard to the reliability of measured values. This reliability factor is a value to be used as reference when deciding whether or not a measured value can be considered reliable, and may be, for instance, a numerical value that indicates the degree to which individual measured values are allowable to be a reliable measurement result with respect to the change in ideal measured values which is determined based upon a plurality of measured values. The operator makes a decision in regard to the reliability of the measured values by referring to this reliability factor to determine whether or not the measuring operation should be terminated. It is to be noted that an example of subjective eye refractive power measuring apparatuses that automatically calculate and display such a reliability factor is disclosed in Japanese Unexamined Patent Publication No. H2-124133.

However, various problems arise with subjective eye refractive power measuring apparatuses in the prior art in which the judgement as to whether or not a measuring operation is to be terminated is left to the operator's discretion.

Namely, an inexperienced operator may not be capable of making an accurate judgement as to when to terminate a measuring operation, which will result in the measuring operation being terminated before a sufficient number of measurements have been performed or while the measured values are still unstable. Or, in some cases, an unnecessarily large number of measurements may be performed, subjecting the subject to the burden of an unnecessarily long examination.

In addition, there is a problem in that, since it is left to the individual operator's discretion when to terminate a measuring operation, measured values may vary among operators and, consequently, the measured values cannot be considered as objective numerical values. Furthermore, even when a subjective eye refractive power measuring apparatus capable of displaying a reliability factor is employed, since the alignment state is unstable, particularity in a hand-held subjective eye refractive power measuring apparatus, the concentration of the operator tends to be focused on correctly maintaining the alignment state and, consequently, a considerable level of skill and experience is required of the operator to be able to perform measurement while checking the reliability factor.

SUMMARY OF THE INVENTION

An object of the present invention is to provide a subjective eye refractive power measuring apparatus that is capable of automatically determining whether or not a measuring operation is to be terminated and obtaining objective and accurate measured values with ease.

In order to achieve the object described above, the subjective eye refractive power measuring apparatus for objectively measuring the optical performance (refractive power or surface curvature) of an optical system to be is tested according to the present invention comprises a measuring optical system including a measuring element that outputs a detection signal which corresponds to the refractive power of the optical system to be tested, an arithmetic device that calculates a measured value related to the optical performance based upon the output signal from the measuring element, a determination or a judgement device that determines whether or not specific conditions related to termination of the measuring operation are satisfied based upon, at least, either the measured values calculated by the arithmetic device or the length of measuring time required for the measuring operation and a termination device that performs specific control for terminating the measuring operation when the determination device has determined that the specific conditions are satisfied.

The determination device may include a validity condition judgment device that judges whether or not a measured value calculated at the arithmetic device satisfies specific validity conditions for recognizing the measured value as valid and a termination condition judgment device that judges whether or not specific termination conditions for terminating the measuring operation are satisfied based upon, at least, either a measured value that has been judged to be valid by the validity condition judgment device or a measured value that has been judged to be not valid by the validity condition judgment device.

It is desirable that the subjective eye refractive power measuring apparatus according to the present invention be further provided with a means for alignment measurement that outputs a signal corresponding to the alignment state of the measuring optical system relative to the optical system to be tested. In this configuration, the validity condition judgment device may include at least one of the following: an alignment validity judgment device that judges whether or not the alignment state of the measuring optical system relative to the optical system to be tested is correct based upon an output signal from the means for alignment measurement when obtaining a measured value at the arithmetic device, a plus/minus judgment device that judges whether or not a measured value obtained by the arithmetic device is negative relative to a measured value obtained immediately before it, a fluctuation judgment device that judges whether or not a measured value obtained by the arithmetic device is within a specific range relative to a reference value calculated based upon measured values obtained before the measured value, an alignment fluctuation judgment device that judges whether or not a change in the alignment state observed after a measured value is obtained relative to the alignment state before the measured value is obtained is within a specific range based upon an output signal from the means for alignment measurement when the measured value has been obtained by the arithmetic device and a reliability factor judgment device that judges whether or not a reliability factor calculated from values provided by the arithmetic device is within a specific range. The validity condition judgment device structured as described above judges that the validity conditions are satisfied when the results of judgments made by all the judgment devices constituting the validity condition judgment device satisfy the individual conditions.

The termination condition judgment device may include, at least, one of the following: a valid measurement number judgment device that judges whether or not the number of measurements that have been judged to be valid by the validity condition judgment device has reached a specific value, a valid value fluctuation judgment device that judges whether or not a measured value that has been judged to be valid by the validity condition judgment device is within a specific range and a time judgment device that judges whether or not the measured value that has been judged to be valid by the validity condition judgment device has been obtained within a specific length of measurement time. The termination condition judgment device structured as described above judges that termination conditions are satisfied when the results of judgments made by all the judgment devices constituting the termination condition judgment device satisfy the individual conditions.

According to the present invention described above, since determination or judgment in regard to condition for whether or not to terminate a measuring operation is made automatically and the measuring operation is automatically terminated if the condition is satisfied, the operator can concentrate entirely on the alignment with the subject without having to keep track of measured values, the number of measurements that have been performed and the like, so that the operation is further facilitated.

In addition, errors introduced by the operator can be eliminated from the process of judging whether or not to terminate a measuring operation and the operation can be performed in an objective manner so that even when measurement is performed by a plurality of operators, the results will be consistent. Furthermore, since a measuring operation will not be terminated prematurely, it can be performed even more accurately.

The termination condition judgment device described above may include, at least, either a defective measurement number judgment device that judges whether or not the number of defective measurements that have been judged to be not valid by the validity condition judgment device has reached a specific value or a time judgment device that judges as to whether a measuring operation could not be terminated within a specific length of measurement time. The termination condition judgment device structured as described above makes a judgment on the termination conditions based upon the results of the judgment made by either one of the judgment devices.

It is desirable that the subjective eye refractive power measuring apparatus according to the present invention be further provided with a means for storage that stores in memory measured values that have been judged to be not valid by the validity condition judgment device among measured values obtained by the arithmetic device as defective values. In this case, the termination device outputs the defective values stored in the means for storage and terminates the measuring operation at least either when the defective measurement number judgment device has judged that the number of defective measurements has reached the specific value or when the time judgment device has judged that the measuring operation could not be terminated within a specific length of measurement time.

Alternatively, the termination device may output a warning and terminate a measuring operation either when the defective measurement number judgment device has judged that the number of defective measurements has reached a specific number or when the time judgment device has judged that the measuring operation could not be terminated within a specific length of measurement time.

According to the present invention described above, a measuring operation is terminated when, for instance, the number of measurements resulting in measured values that have been judged to be not valid by the validity condition judgment device has reached a specific number and a measuring operation can be automatically terminated in a suitable manner in the event of an error. Thus, it is possible to prevent an excessive time burden from being imposed on the subject.

It is desirable that the subjective eye refractive power measuring apparatus according to the present invention be further provided with a means for condition relaxation that relaxes conditions used by the judgment devices for making validity judgments on, at least, one of the following occasions: when the defective measurement number judgment device has judged that the number of defective measurements has reached a specific value, when the valid value fluctuation judgment device has judged that a measured value that has been judged to be valid is outside a specific range and when the time judgment device has judged that a measuring operation could not be terminated within a specific length of measurement time. Such a means for condition relaxation effects relaxation of conditions by increasing the specific value set at the defective measurement number judgment device, expanding the specific range set at the valid value fluctuation judgment device and extending a specific length of measurement time set at the time judgment device.

According to the present invention described above, by relaxing the conditions used by the individual judgment devices, consistent measurement results can be obtained even when an abnormality is observed in the measured values.

It is even more desirable that the subjective eye refractive power measuring apparatus according to the present invention be further provided with a condition setting device for freely setting specific conditions related to termination of a measuring operation.

According to the present invention described above, since specific conditions related to termination of a measuring operation can be freely set, automatic measurement termination control that corresponds to the operating state can be implemented by, for instance, making judgements on fluctuations in the alignment using relaxed conditions at an optometry clinic where many patients are children whose eye movement tends to be active.

Alternatively, the subjective eye refractive power measuring apparatus according to the present invention may be further provided with a fixation target indicator device that indicates the fixation target to the subject. The fixation target indicator device changes the movement of the fixation target when the termination condition judgment device has judged that the specific conditions related to termination of a measuring operation are not satisfied.

According to the present invention described above, by changing the movement of the fixation target when the specific conditions related to termination of a measuring operation are not satisfied, a measuring operation in an improved state, in which more stable fixation is achieved if an abnormality is observed in measured values.

The subjective eye refractive power measuring apparatus according to the present invention for objectively measuring the optical performance of an optical system to be tested comprises a measuring element that outputs a signal corresponding to the optical performance of the optical system to be tested, an arithmetic device that calculates a measured value related to the optical performance based upon the output signal from the measuring element and a mode switching device that switches between a manual measurement mode, in which a measuring operation is started and terminated based upon the judgment of the operator, and an automatic measurement mode, in which a measuring operation is started and terminated through automatic judgment.

By making it possible to switch between the automatic measurement mode and the manual measurement mode as in the present invention, a lesser degree of burden is placed upon the subject who is expected to manifest abnormality in measured values by selecting in advance the manual measurement mode.

DETAILED DESCRIPTION OF THE PREFERRED EMBODIMENTS

Figure 1:
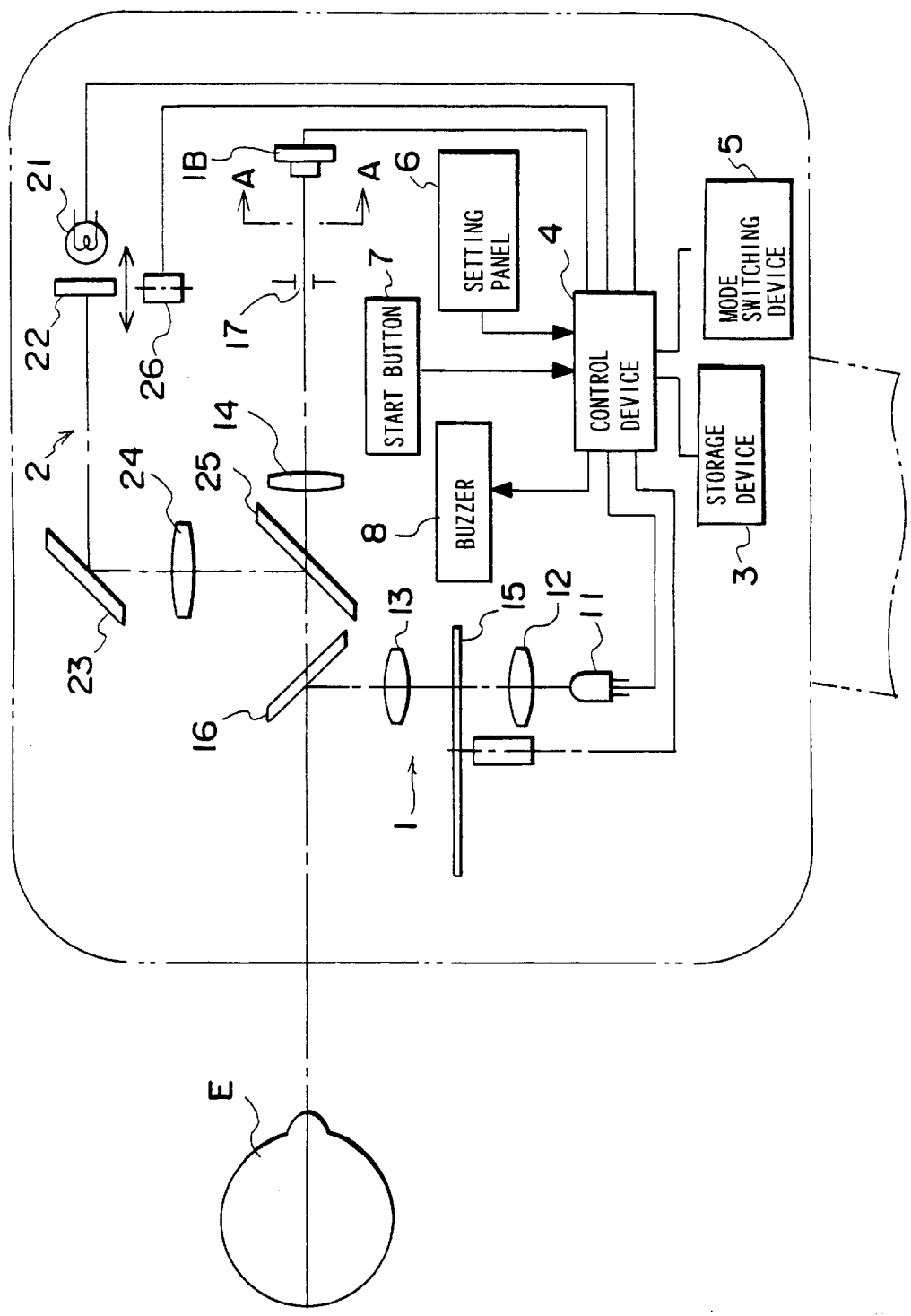
FIG. 1 illustrates the optical structure of the subjective eye refractive power measuring apparatus in a first embodiment of the present invention, viewed from the side.
Figure 2:
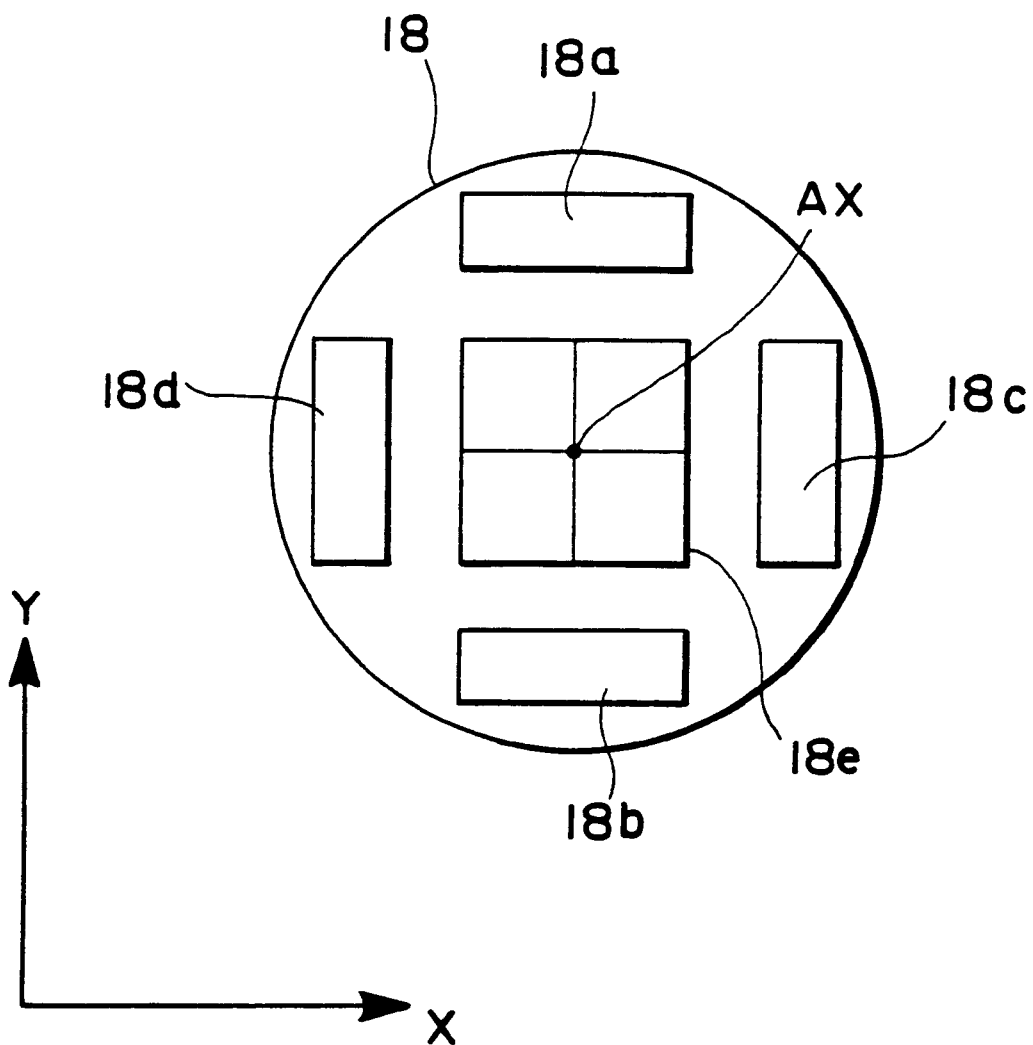
FIG. 2 is a cross section along line A—A in FIG. 1.
Figure 3:
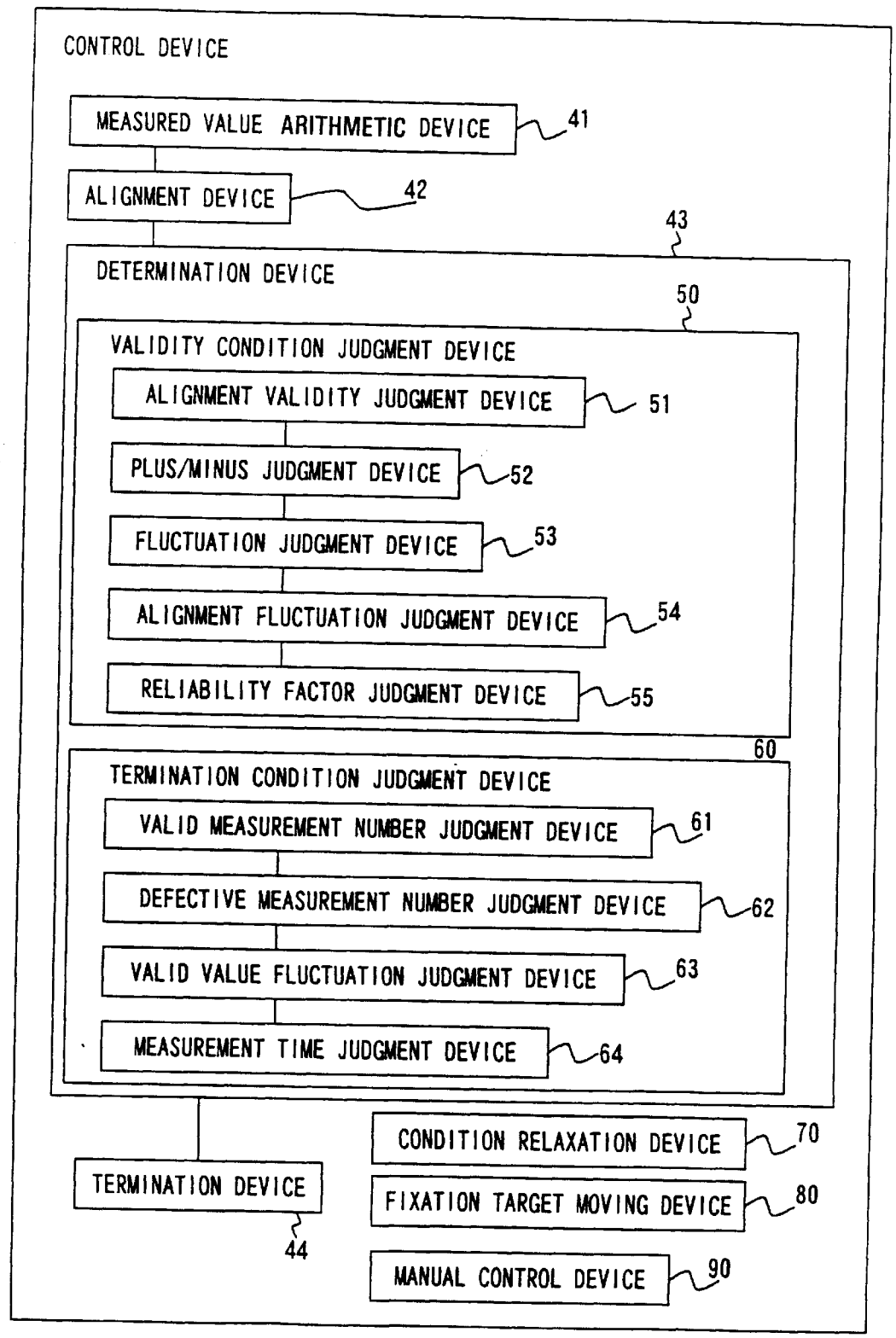
FIG. 3 is a functional block diagram of the control device in the subjective eye refractive power measuring apparatus in the first embodiment.
Figure 4A:
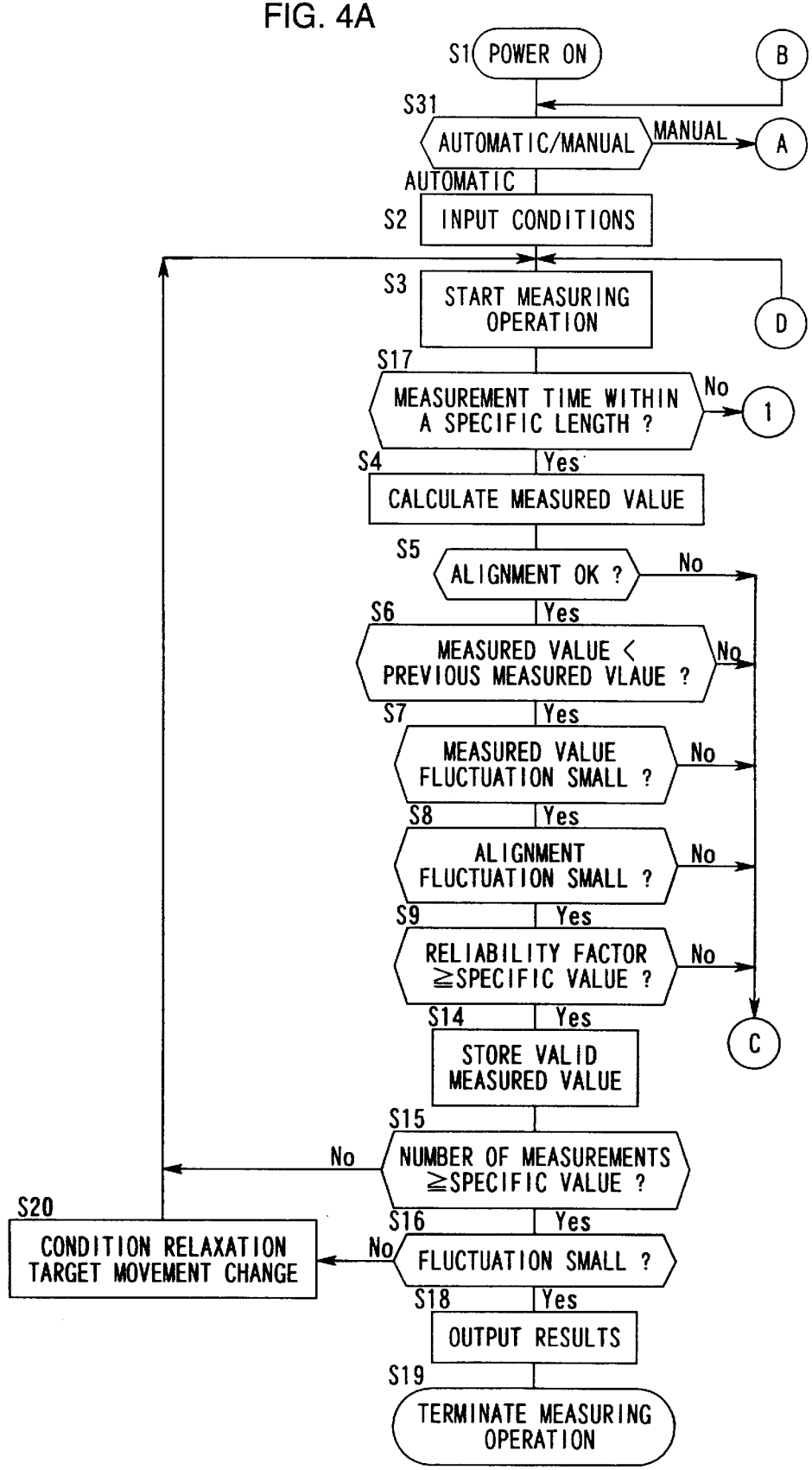
FIGS. 4A and 4B are flowcharts illustrating a measuring operation performed by the subjective eye refractive power measuring apparatus in the first embodiment.
Figure 4B:
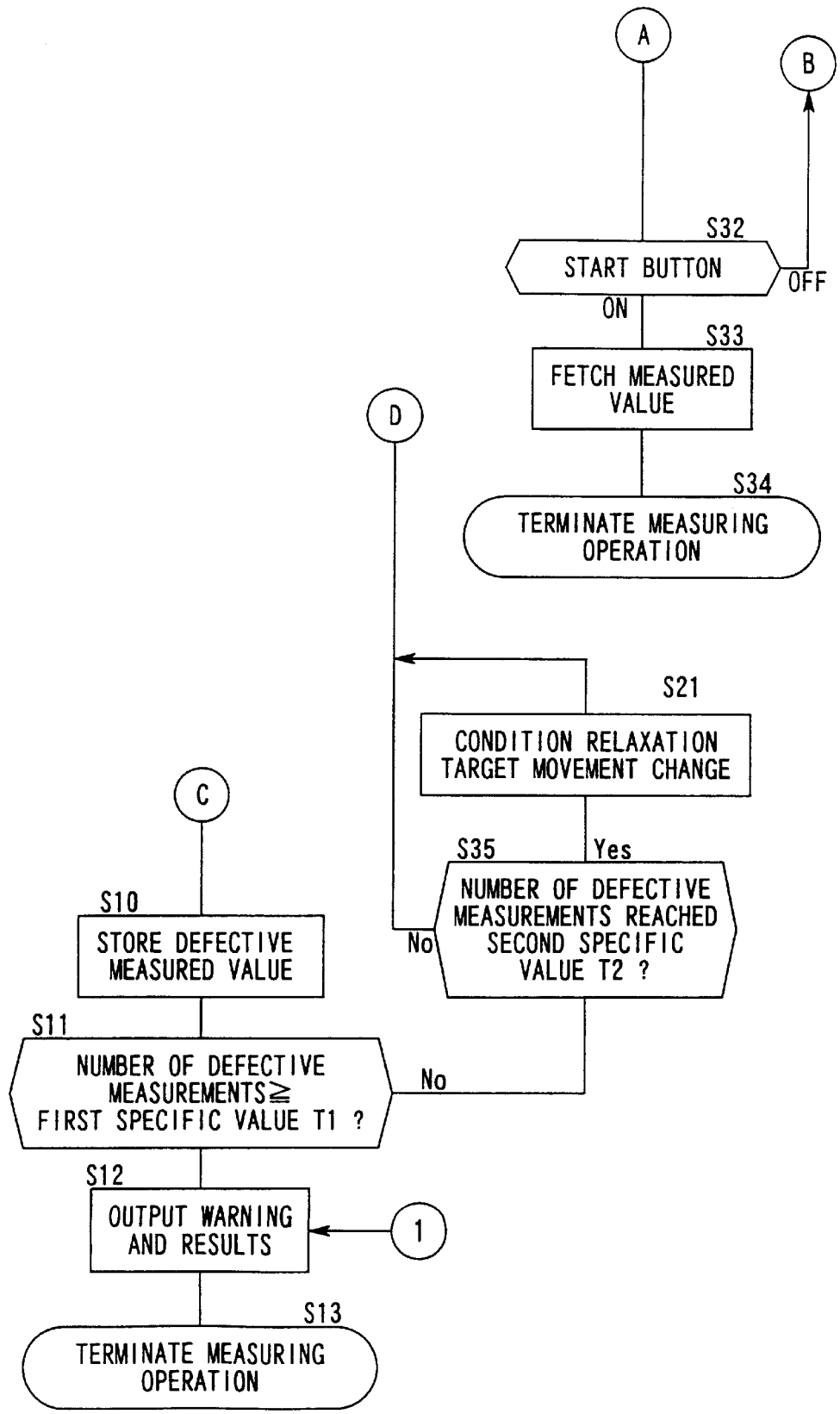

The following is a detailed explanation of the first embodiment of the subjective eye refractive power measuring apparatus according to the present invention, given in reference to the drawings. FIG. 1 illustrates the optical structure of the subjective eye refractive power measuring apparatus viewed from the direction of a side surface, FIG. 2 is a cross section along line A—A in FIG. 1, FIG. 3 is a functional block diagram illustrating in detail the electrical structure of the control device of the subjective eye refractive power measuring apparatus and FIGS. 4A and 4B are flowcharts of the measuring operation performed by the subjective eye refractive power measuring apparatus.

It is to be noted that while the explanation is given on an example in which the present invention is adopted in a hand-held subjective eye refractive power measuring apparatus in reference to this embodiment, the present invention may be adopted in a stationary subjective eye refractive power measuring apparatus in a similar manner. In addition, while the optical system to be tested is an eye E in the explanation, the present invention may be adopted when testing all types of test optical systems other than eyes.

First, the structure of the subjective eye refractive power measuring apparatus is explained and then the measuring operation performed by the subjective eye refractive power measuring apparatus will be explained. As shown in FIG. 1, the subjective eye refractive power measuring apparatus is constituted by providing inside a casing, a measurement device 1 for objectively measuring the optical performance of an eye E to be tested, such as its refractive power or curvature of surface, a fixation optical system 2 for fixating the eye E to be tested in a specific direction, a storage device 3, a control device 4 for controlling the measurement device 1, the fixation optical system 2 and the storage device 3, a mode switching device 5 for switching between a manual measurement mode and an automatic measurement mode, a setting panel 6 that is employed to set various conditions and is provided with a liquid crystal display device for displaying the setting details, measured values and the like, a start button 7 for starting a measuring operation and a warning buzzer 8. When the automatic measurement mode is selected by the mode switching device 5, an instruction for automatic measurement is issued by pressing the start button 7, and when it is determined that the correct alignment has been achieved, the measuring operation is automatically started. Then, when it is decided that the measuring operation should be terminated, the series of measurements is automatically terminated. When the manual measurement mode has been selected, a measuring operation starts when the operator presses the start button 7.

The measurement device 1, which is structured similarly to that in subjective eye refractive power measuring apparatuses in the prior art, projects a measurement light onto the eye E to be tested and receives the measurement light reflected by the eye E to measure the optical characteristics of the eye E such as its refractive power. In more specific terms, the measurement device 1 is provided with an infrared light source 11, lenses 12~14, a chopper 15, a half mirror 16, an aperture 17 and a light sensor 18. A measurement light emitted from the infrared light source 11 travels through the lens 12 to be scanned by the chopper 15, and the scanned measurement light is then guided to the eye E to be tested via the lens 13 and the half mirror 16. The measurement light that is then reflected by the eye E to be tested travels through the half mirror 16, the lens 14 and the aperture 17 to be received by the light sensor 18.

The light sensor 18 is constituted of four photoelectric conversion elements 18a~8d and a 4-division photosensitive element 18e. The four photoelectric conversion elements 18a~18d are employed to measure the optical characteristics of the eye E to be tested. The 4-division photosensitive element 18e is employed to measure the alignment state of the eye E to be tested, and a measuring operation automatically starts when it is decided that the alignment have been completed in the automatic measurement mode.

The 4-division photosensitive element 18e is divided into four portions along the X axis and the Y axis passing through the central axis AX of the light sensor 18, with the individual divided element portions provided at uniform positions above and below and to the left and right around the optical axis in FIG. 2. Signals from the individual divided element portions of the 4-division photosensitive element 18e are output to an alignment judgement device 42, which is to be detailed later, of the control device 4. At the alignment judgement device 42, a judgement is made as to whether or not the alignment state of the eye E to be tested is correct relative to the measuring optical system of the subjective eye refractive power measuring apparatus based upon differences among the quantities of measurement light received at the individual element portions of the 4-division photosensitive element 18e. When a measurement light enters the central area of the 4-division photosensitive element 18e, the measurement light is received at the individual divided element portions, and with the output signals from the individual element portions almost equal to one another, it is judged that the alignment is correct. Thus, the light sensor 18 is positioned in such a manner that the central axis AX of the 4-division photosensitive element 18e is aligned with the optical axis of the measurement device 1.

A pair of photoelectric conversion elements 18a and 18b are positioned symmetrically to each other in the direction of the Y axis across the central axis AX to measure the intervals in the stripe pattern formed by the measurement light scanned in the direction of the Y axis. The photoelectric conversion elements 18c and 18d, which are positioned symmetrically to each other in the direction of the X axis over the central axis AX, measure the intervals in the striped pattern formed by the measurement light scanned in the direction of the X axis. When the measurement light is received at the photoelectric conversion elements 18a~18d, signals are output to a measured value arithmetic device 41, which is to be detailed later, of the control device 4 from the photoelectric conversion elements 18a~18d. At the measured value arithmetic device 41, a measured value in the direction of the Y axis is calculated based upon the difference between the phases of the measurement light received at the pair of photoelectric conversion elements 18a and 18b and a measured value in the direction of the X axis is calculated based upon the difference between the phases of the measurement light received at the pair of photoelectric conversion elements 18c and 18d.

The fixation optical system 2 is constituted with a visible light source 21, a fixation target 22, a total reflection mirror 23, a lens 24 and a dichroic mirror 25 which reflects visible light and transmits infrared light. Fixation light that has been emitted by the visible light source 21 and has been transmitted through the fixation target 22 is then projected onto the eye E to be tested via the total reflection mirror 23, the lens 24 and the dichroic mirror 25. The fixation target 22, which can be moved by a motor 26 in the direction of the optical axis of the fixation optical system 2, is caused to move by the control device 4 to a position at which the eye E to be tested can fixate in conformance to a measured value of the eye E.

The storage device 3 stores in memory a measured value which has been output together with a "signal indicating that the measured value is not valid" from a validity condition judgment device 50, which is to be detailed later, as a defective value and also stores in memory a measured value that has been output together with a "signal indicating that the measured value is valid" from the validity condition judgment device 50 as a valid value. In addition, the storage device 3 stores in memory an output value, output from the 4-division photosensitive element 18e, and a specific reference value, a specific reference number and a specific range that are set as judgement criteria used by various judgement portions within the validity condition judgment device 50 and a termination condition judgement device 60 which is to be detailed later. More specifically, the storage device 3 is constituted of a RAM. However, it may be constituted of another electronic storage medium, a magnetic storage medium or an optical storage medium instead. The specific reference value, the specific number and the specific range stored in memory at the storage device 3 can be freely changed through the setting panel 6 mentioned earlier.

The control device 4 may be constituted of a CPU, a ROM, a RAM and peripheral circuits, and various types of processing are implemented by executing a program that is stored in advance in the ROM. The functions of the control device 4 that are executed by the programs are explained in reference to the functional block diagram in FIG. 3. The control device 4, which is provided with the measured value arithmetic device 41 and the alignment device 42 each mentioned earlier, controls the measurement device 1, the fixation optical system 2, the storage device 3 and a liquid crystal display device (not shown) on the setting panel 6.

In the subjective eye refractive power measuring apparatus in this embodiment, when the start button 7 is pressed in the manual measurement mode, the output signals from the photosensitive elements 18a~18d are read and various measured values are calculated regardless of the state of the alignment. A manual measurement device 90 is provided for this reason.

If the start button 7 is pressed in the automatic measurement mode, the alignment judgement performed at the alignment device 42 is monitored, and when a correct alignment state is achieved, a measuring operation automatically starts. Thus, the control device 4 is provided with a judgement device 43 that determines whether or not specific conditions in regard to a measurement end are satisfied based upon the measured values provided by the light sensor 18 of the measurement device 1 and a termination device 44 that implements specific control for terminating a measuring operation when the judgement device 43 has determined that the specific conditions are satisfied, as illustrated in FIG. 3.

At the judgement device 43, first a decision is automatically made as to whether or not a measured value is valid in order to determine whether or not the measurement has been performed correctly, and then based upon the results of the decision-making, the correctness of the measurement is determined. Thus, the judgement device 43 is provided with a validity condition judgment device 50 that judges whether or not specific validity conditions for recognizing a measured value obtained by the measurement device 1 as valid are satisfied and a termination condition judgement device 60 that judges whether or not specific termination conditions for terminating the measuring operation are satisfied based upon the measured values that have been judged to be valid by the validity condition judgment device 50, as illustrated in FIG. 3.

The specific validity conditions are constituted of a plurality of conditions for determining the validity of a measured value. In order to make a judgement on each of the plurality of conditions, the validity condition judgment device 50 is provided with an alignment validity judgment device 51 that judges whether or not the alignment state of the apparatus relative to the eye E to be tested has been correct when a measured value is obtained by the measurement device 1, a plus/minus judgment device 52 that judges whether or not a measured value obtained by the measurement device 1 is negative relative to a measured value obtained immediately before the measured value, a fluctuation judgement device 53 that judges whether or not a measured value obtained by the measurement device 1 is within a specific range relative to a reference value which has been calculated based upon measured values obtained before the measured value, an alignment fluctuation judgement device 54 that judges whether or not the change in the alignment state occurring after a measured value is obtained by the measurement device 1 relative to the state before the measured value is obtained is within a specific range and a reliability factor judgement device 55 that judges whether or not a reliability factor calculated based upon the measured values obtained by the measurement device 1 is within a specific range, as illustrated in FIG. 3.

Each time a measured value is input, the alignment validity judgement device 51 takes in the outputs from the individual divided element portions of the 4-division photosensitive element 18e at the point in time at which the input occurs and based upon the outputs, it judges whether or not a correct alignment state has been achieved in a manner similar to that in which the alignment device 42 mentioned earlier performs decision-making. Then, if the alignment state is judged to be correct, it decides that the measured value is valid and outputs the measured value to the plus/minus judgment device 52. If the alignment state is determined to be incorrect, it decides that the measured value is not valid and outputs the measured value to the storage device 3 together with the "signal indicating that the measured value is not valid."

The judgement is made by the alignment validity judgement device 51 as described above for the following reason. Namely, a slight lapse of time occurs after the alignment device 42 of the control device 4 determines that the alignment state is correct until the actual measurement is taken, and during this slight lapse of time, the eye E to be tested may move to cause the alignment state to become incorrect. Because of this, a judgement is made as to whether or not a measured value is valid by verifying the alignment state with the alignment validity judgement device 51 at the very moment when the measurement is taken, i.e., at the moment when the measured value is calculated.

Each time a measured value is input, the plus/minus judgment device 52 calls up a measured value that has been calculated and judged to be valid immediately before the measured value is input, i.e., the measured value that has been most recently stored in memory among the measured values stored in the storage device 3 as valid values and compares the called-up measured value and the input measured value to determine their negative/positive relationship. Then, it judges that the input measured value is valid if it is equal to or plus relative to the called-up measured value and outputs it to the fluctuation judgement device 53. If, on the other hand, the input measured value is minus relative to the called-up measured value, it judges that the measured value is not valid and outputs the measured value to the storage device 3 together with a "signal indicating that the measured value is not valid." For instance, while if the input measured value is "−2.5D" relative to the called-up measured value at "−3D," the measured value "−2.5D" is judged to be valid, if the input measured value is "−5D," the measured value "−3.5D" is judged to be not valid. In addition, if the input measured value is "3.5D" relative to the called-up measured value of "3D," the measured value "3.5D" is judged to be valid, whereas if the input measured value is "2.5D," the measured value "2.5D" is judged to be not valid.

It is to be noted that in the plus/minus judgment device 52, the comparison is implemented by using the spherical power (spherical power factor) S among the measured values, and if a cylindrical power factor C is available the equivalent spherical power (equivalent spherical power factor) is calculated through (S+C/2) to be used in the comparison.

The judgement is made as described above by the plus/minus judgment device for the following reason. Namely, if a newly input measured value is minus relative to the immediately preceding measured value, it is likely that an adjustment of visual acuity has occurred at the eye E to be tested for some reason. In other words, it is likely that the optical characteristics of the eye E to be tested have changed. Thus, the plus/minus judgment device 52 compares the plus/minus to make a judgement as to whether or not the measured value is valid.

Each time a measured value is input, the fluctuation judgement device 53 calls up all the measured values that have been stored in memory as valid values since the start of the measuring operation up to the current point in time from the storage device 3 and calculates an average value of the called-up measured values. Then it compares the calculated average values against the input measured value and judges whether or not the difference between them is within the specific range (for instance ±0.3 diopters). If the difference is within a specific range, the measured value is judged to be valid and is output to the alignment fluctuation judgement device 54. If, on the other hand, the difference is not within a specific range, the measured value is judged to be not valid and is output to the storage device 3 together with a "signal indicating that the measured value is not valid."

The judgement is made as described above by the fluctuation judgement device 53 for the following reason. Namely, when a measured value has fluctuated greatly, it is likely that there has been a problem (for instance, the subject has blinked, the eye E to be tested has made a gross movement, there has been a partial abnormality in the eye E to be tested or the like). For this reason, the fluctuation judgement device 53 verifies the state of fluctuation of the measured value to make a judgement as to whether or not the measured value is valid.

Each time a measured value is input, the alignment fluctuation judgement device 54 monitors the fluctuation of the alignment state occurring over the course of the measurement of the value. More specifically, the output value output by the 4-division photosensitive element 18e is stored in the storage device 3 and the stored output value is held until a specific length of time elapses. Each time a measured value is input, the alignment fluctuation judgement device 54 calls up a specific number of output values from the 4-division photosensitive element 18e starting with the most recent output value, among the output values from the 4-division photosensitive element 18e stored in the storage device 3 at a point in time at which a specific length of time has elapsed since the input.

A specific length of time and the specific number are set to ensure that the same number of output values preceding and following the point in time at which the measured value is input are called up. For instance, at a point 0.1 seconds after an input, ten output values stored in the storage device 3 are called up starting with the most recent output value so that five output values preceding the input of the measured value and five output values following the input are called up. The alignment fluctuation judgement device 54 calculates the average value of the specific number of output values thus called up and judges whether or not the average value is within a specific range. If the average value is within the specific range, it is judged that the measured value is valid and the measured value is output to the next reliability factor judgement device 55, whereas if it is not within the specific range, the measured value is judged to be not valid and is output to the storage device together with a "signal indicating that the measured value is not valid."

The judgement is made by the alignment fluctuation judgement device 54 as described above for the following reason. Namely, when there is a large difference between in the alignment state before and after the measurement, it is likely that the alignment state has become momentarily correct while the eye E to be tested is making an abrupt movement to cause the measurement to take place with the fixation of the eye E still incomplete. Since the objectives of the fixation of the eye E include elimination of a visual acuity adjustment of the eye E and it is likely that a visual acuity adjustment of the eye E has occurred when the fixation of the eye E has not been completed, the fluctuation of the alignment state is verified by the alignment fluctuation judgement device 54 to make a judgement as to whether or not the measured value is valid.

Each time a measured value is input, the reliability factor judgement device 55 calculates the reliability factor of the input measured value and judges whether or not the reliability factor is equal to or greater than a specific factor. Then, if it is equal to or greater than the specific factor, the measured value is judged to be valid, and the measured value is output to the storage device 3 together with the "signal indicating that the measured value is valid,", whereas if it is less than the specific factor, the measured value is judged to be not valid and the measured value is output to the storage device 3 together with a "signal indicating that the measured value is not valid."

It is to be noted that the reliability factor itself is calculated in a manner similar to that employed in the prior art and, for instance, it is obtained by calculating an ideal measured value based upon all the measured values stored in the storage device 3 at the current point in time and calculating the difference between the ideal measured value and the actual measured value that has been taken.

The judgement is made by the reliability factor judgement device 55 as described above for the following reason. Namely, as in the prior art, the reliability factor is provided as a reference for determining the reliability of a measured value, and the reliability of the measured value is considered to be low if the reliability factor is low. Thus, the reliability factor judgement device 55 verifies the reliability factor of the measured value to make a judgement as to whether or not the measured value is valid.

Next, the termination condition judgement device 60 is explained. The specific termination conditions for which judgements are made by the termination condition judgement device 60 are constituted of a plurality of conditions for deciding whether or not the measuring operation should be terminated. In order to make a judgement on each of the plurality of conditions, the termination condition judgement device 60 is provided with a valid measurement number judgement device 61 that judges whether or not the number of measured values that have been judged to be valid by the validity condition judgment device 50 has reached a specific value, a defective measurement number judgement device 62 that judges whether or not the number of measured values that have been determined to be not valid by the validity condition judgment device 50 has reached a specific value, a valid value fluctuation judgement device 63 that judges whether or not a measured value that has been determined to be valid by the validity condition judgment device 50 is within a specific fluctuation range and a measurement time judgement device 64 that judges whether or not the time that has elapsed since the measurement start is within a preset specific length of time, as illustrated in FIG. 3.

The valid measurement number judgement device 61 totals the number of times a measured value has been stored as a valid value (the number of valid measurements), each time a measured value is stored in the storage device 3 as a valid value. Each time a new totaled value is calculated, a judgement is made as to whether or not the latest totaled value is equal to or greater than a specific value for valid measurement and if it is judged to be equal to or greater than the specific value, an "prompt signal" for prompting judgement by the valid value fluctuation judgement device 63 is output to the valid value fluctuation judgement device 63. If the totaled value is under the specific value, a "sustain signal" for continuing the measuring operation is output to the measured value arithmetic device 41.

The judgement is made by the valid measurement number judgement device 61 as described above for the following reason. Namely, if the number of measured values that have been judged to be valid by the validity condition judgment device 50 is small, it is likely that the reliability of a judgement made by the fluctuation judgement device 53 or the reliability factor judgement device 55 of the validity condition judgment device 50 or a judgement made by a valid value fluctuation judgement device 63, which is to be detailed later, is low. Thus, the number of measurements of valid measured values is verified by the valid measurement number judgement device 61 to make a judgement as to whether or not the measuring operation may be terminated.

The defective measurement number judgement device 62 totals the number of times a measured value has been stored as a defective value (the number of defective measurements), each time a measured value is stored in the storage device 3 as a defective value. Each time a new totaled value is calculated, a judgement is made as to whether or not the latest totaled value is equal to or greater than a specific value for detective measurement, and if it is judged to be equal to or greater than the specific value, a "error end signal" for terminating the measuring operation in an error is output to the termination device 44, whereas if it is judged to be smaller than the specific value, a "sustain signal" for sustaining the measuring operation is output to the measured value arithmetic device 41.

The judgement is made by the defective measurement number judgement device 62 as described above for the following reason. Namely, since there are states that are unique to a given eye E to be tested, the measuring operation may not be terminated due to lack of valid measured values even after a specific number of measurements have been performed. In such a case, it is highly likely that there is an abnormality in the eye E to be tested or the apparatus itself, and thus, it would be useless to simply continue with the measuring operation which would only increase the burden on the subject. For this reason, the defective measurement number judgement device 62 is employed to monitor the number of measurement of measured values that have been determined to be not valid by the validity condition judgment device 50, so that a signal can be output to the termination device 44 as necessary to terminate the measuring operation.

Each time an "prompt signal" is input from the valid measurement number judgement device 61, the valid value fluctuation judgement device 63 calls up all the measured values that have been stored in the storage device 3 as valid values, calculates the equivalent spherical power of each measured value and then calculates a statistic value (for instance, a standard deviation) that indicates dispersion of the equivalent spherical powers. Then, if this statistic value is within a specific range, it outputs a "normal end signal" for terminating the measuring operation normally to the termination device 44, whereas if the statistic value indicating dispersion of the equivalent spherical powers is not within the specific range, a "sustain signal" for continuing with the measuring operation is output to the measured value arithmetic device 41.

The judgement is made by the valid value fluctuation judgement device 63 as described above for the following reason. Namely, when the equivalent spherical powers demonstrate a gradual increase, it is likely that a visual acuity adjustment of the eye E to be tested is being taken place. In addition, when the degree of inconsistency among the equivalent spherical powers is large, too, it is likely that the visual acuity adjustment of the eye E has not been completed yet, as in the case described above. Thus, the valid value fluctuation judgement device 63 is employed to verify inconsistency among the equivalent spherical powers to make a judgement as to whether or not the measuring operation should be terminated. It is to be noted that the judgement may be implemented based upon inconsistency in the spherical powers S or the cylindrical powers C instead of the inconsistency in the equivalent spherical powers, and that any statistic value other than the standard deviation, that can be used to judge the stability of the measured values may be employed instead.

In addition, the measurement time judgement device 64 counts the length of measurement time elapsing from the measurement start. By combining this count and the measurement, an "error end signal" indicating that the measuring operation cannot be performed is output to the termination device 44 to forcibly end the measuring operation if valid measured values cannot be obtained within a specific length of time that is set arbitrarily. If valid measured values can be obtained within a specific length of time that is set arbitrarily, a "normal end signal" is output to the termination device 44.

The judgement is made by the measurement time judgement device 64 as described above for the following reason. Namely, there are states that are unique to a given eye E to be tested and if there is a degree of turbidity, a scar or the like in the transparent portion of the eye, the measurement may be impossible since no reflected light from the eye ground can be obtained. In such a case, proper measurement cannot be performed no matter how long the measuring operation is continued, and thus, in order to avoid placing an unnecessary burden on the subject, the operation is terminated within a specific length of time since no proper measurement is possible.

Next, the termination device 44 is explained. The termination device 44 controls the various portions within the apparatus using the settings that are selected in advance, in correspondence to a signal output by the termination condition judgement device 60 of the judgement device 43 to terminate the measuring operation. More specifically, when a "normal end signal" is output from the termination condition judgement device 60, it outputs all the measured values stored in the storage device 3 as valid values onto a printer (not shown), initializes the contents of the storage in the storage device 3 and terminates the measuring operation.

If an "error end signal" is output from the termination condition judgement device 60, all the measured values that have been stored in the storage device 3 as valid values and all the measured values that have been stored in the storage device 3 as defective values are output to a printer (not shown), the buzzer 8 is sounded for a specific length of time and the memory contents in the storage device 3 are initialized before terminating the measuring operation.

While presented are no specific numerical values for the specific ranges, the specific values and the specific reference values that are used for criteria in the judging performed by the alignment validity judgement device 51, the plus/minus judgment device 52, the fluctuation judgement device 53, the alignment fluctuation judgement device 54, the reliability factor judgement device 55, the valid measurement number judgement device 61, the defective measurement number judgement device 62 and the valid value fluctuation judgement device 63, arbitrary numerical values may be set for them based upon values obtained through experience.

In addition, the control device 4 is provided with a condition relaxation device 70 and a fixation target moving device 80. The condition relaxation device 70 is provided to relax the judgement criteria used at the judgement devices mentioned above and to allow a measuring operation to be performed over a long period of time when the number of defective measurements is equal to or exceeds a specific value in order to ensure that a calculated measured value is not too readily judged to be defective. The fixation target moving device 80 is provided to move the fixation target 22 to a position at which the eye E to be tested cannot achieve a visual acuity adjustment in case that the number of defective measurements is equal to or exceeds the specific value or that valid values fluctuate greatly. In either case, the refractive power of the eye E to be tested is considered to be adjusted during measurements.

The measuring operation performed by the subjective eye refractive power measuring apparatus in this embodiment is explained in reference to FIGS. 4A and 4B. It is to be noted that this flowchart does not necessarily present only the procedure executed by the CPU but also presents the procedure carried out through the operator's operation.

When the power supply of the subjective eye refractive power measuring apparatus is turned on, a series of processing starts (step S1). In step S31, a judgement is made as to whether the automatic measurement mode or the manual measurement mode has been selected. If the manual measurement mode has been selected, a judgement is made in step S32 in regard to the operation of the start button 7. If it is decided in step S32 that the start button 7 has been operated, output signals from the photosensitive elements 18a~18e are read and stored in a specific storage area in step S33. Then, using the stored measurement signals, various types of calculation are executed and the measured values are output.

If the automatic measurement mode has been selected, the operation awaits an input of the measurement conditions (ex. specific ranges) mentioned earlier via the setting buttons on the setting panel 6 (step S2). It is to be noted that since the values representing the measurement conditions used in the previous measuring operation are held, the operation proceeds to the next step without inputting the specific ranges and the like if the current measuring operation is to be performed under the same conditions as those used in the previous measuring operation. After the start button 7 is operated and an instruction for a measurement start is issued, the measuring operation starts if it is decided by the alignment validity judgement device 51 that the alignment state of the subjective eye refractive power measuring apparatus relative to the eye E to be tested is correct (step S3). If it is judged in step S17 that the length of measurement time is within a specific length of time, the measured value arithmetic device 41, which has received a signal from the light sensor 18, calculates the first measured value (step S4). The length of measurement time refers to the length of time elapsing after the operation of the start button 7.

Various types of judgements are made on the measured value calculated in step S4 by the validity condition judgment device 50 of the control device 4. Namely, the validity of the measured value is judged by the alignment validity judgement device 51, the plus/minus judgment device 52, the fluctuation judgement device 53, the alignment fluctuation judgement device 54 and the reliability factor judgement device 55 (steps S5~S9). If any one of the judgement devices judges that the measured value is not valid, a "signal indicating that the measured value is not valid" is output together with the measured value to the storage device 3 by the judgement device that has made the judgement, and the measured value is stored as a defective value in the storage device 3 (step S10).

If a measured value is stored as a defective value, 1 is added to the total number of measurements in which the measurement results have been judged to be defective, and a judgement is made by the defective measurement number judgement device 62 as to whether the totaled value is equal to or greater than a first specific value T1 (step S11). If the totaled value is not equal to or greater than the first specific value T1, a judgement is made as to whether or not the number of defective measurements is equal to a second specific value T2 (<T1) (step S35), and if the number of defective measurements has not yet reached T2, the operation returns to step S3 to continue the measuring operation under the same conditions. In other words, a "sustain signal" is output to the measured value arithmetic device 41. When the number of defective measurements is judged to have reached the second specific value T2 in step S35, a specific length of time used in step S17 is extended by the condition relaxation device 70 in step S21 to relax the conditions in regard to the length of measurement time. In addition, the fixation target moving device 80 employs a motor 26 to move the fixation target 22 to ensure that the visual acuity adjustment cannot be achieved at the eye E to be tested, and a "sustain signal" is output to the measured value arithmetic device 41.

Now, the purpose of moving the fixation target 22 is explained. The movement of the fixation target 22, which is controlled by the control device 4, is described below. Before moving the fixation target 22, a preliminary measurement is performed, and based upon the preliminary measured value, the fixation target 22 is moved to a position at which the subject can visually recognize the fixation target. The subject is shown the fixation target in advance so that he can recognize the fixation target and use it as a target for his line of sight. Then, the fixation target is moved to a position that achieves a specific value (+2D) relative to the preliminary measured value and is stopped there. The main measuring operation is continuously performed at this position. If the measuring operation is stable, measurements are repeated at the (+2D) state and consequently, the measuring operation is terminated within a short period of time.

However, instability in measured values occurring for any reason, results in a measuring operation that does not satisfy the measurement termination conditions. In some cases it is even possible that the subject cannot see the fixation target 22 at all, which will cause measured values to become unstable. In the apparatus according to the present invention, instead of simply continuing with the measuring operation when the measuring operation does not satisfy the measurement termination conditions, the fixation target 22 is moved in order to stabilize the measuring operation. Namely, in a measuring operation that does not satisfy the measurement operation termination conditions, a series of operations in which the movement of the fixation target 22 is changed to move the fixation target to a position at which it can be seen by the subject and then it is moved to the +2D position is implemented again instead of simply continuing with the measuring operation in the same state. Since this allows the subject to look at the fixation target 22 if the measuring operation is to continue, the target to be fixated upon is made clear, thereby making it possible to perform the measuring operation in a state in which the fixation is more stable.

If it is judged in step S11 that the number of defective measurements is equal to or greater than the first specific value T1, an "error end signal" is output to the termination device 44 by the defective measurement number judgement device 62. This causes the termination device 44 to which the "error end signal" has been input to sound the buzzer 8 and to output all the measured values stored in the storage device 3 as defective values and as valid values via the printer (not shown) (step S12) before terminating the measuring operation (step S13).

If the measured value is judged to be valid in each of the steps S5~S9, a "signal indicating that the measured value is valid" and the measured value are output to the storage device 3 by the reliability factor judgement device 55, and this measured value is stored in the storage device 3 as a valid value (step S14). When a measured value is stored as a valid value in this manner, 1 is added to the total number of measurements in which the measurement results have been determined to be valid, and a judgement is made as to whether or not this totaled value is equal to or greater than a specific value (step S15). If it is smaller than the specific value, a "sustain signal" is output to the measured value arithmetic device 41 and the measuring operation continues with the fixation target 22 remaining at the same position. If, on the other hand, it is equal to or greater than the specific value, a "prompt signal" is output to the valid value fluctuation judgement device 63.

The valid value fluctuation judgement device 63 into which the "prompt signal" has been input calculates an equivalent spherical power and calculates a statistic value indicating inconsistency in the equivalent spherical powers (step S16). If the statistic value is not within a specific range, a signal is output by the valid value fluctuation judgement device 63 to the condition relaxing device 70 and the fixation target moving device 80. The condition relaxation device 70 relaxes the condition imposed in regard to the length of measurement time by extending the specific set time used in step S17. In addition, the fixation target moving device 80 employs the motor 26 to move the fixation target 22 to move the fixation target 22 by "+2D" after it is shown to the subject to be tested to prevent visual acuity adjustment. Then, a "sustain signal" is output to the measured value arithmetic device 41 to continue the measuring operation. If, on the other hand, the statistic value is judged to be within the specific range in step S16, a "normal end signal" is output to the termination device 44. The termination device 44 outputs all the measured values stored in the storage device 3 as valid values via the printer (not shown) (step S18) before terminating the measuring operation (step S19). If the measuring operation continues in the operation described above, the same steps are repeated until the measuring operation is automatically terminated.

The present invention is not limited to the example presented in the embodiment described above, and may be implemented in various different modes without departing from the scope of its technical concept. The following is an explanation of different modes that may be adopted.

First, it is not necessarily essential that all of the judgement devices, i.e., the alignment validity judgement device 51, the plus/minus judgment device 52, the fluctuation judgement device 53, the alignment fluctuation judgement device 54, the reliability factor judgement device 55, the valid measurement number judgement device 61, the defective measurement number judgement device 62, valid value fluctuation judgement device 63 and the measurement time judgement device 64, be provided. Only some of them, arbitrarily selected, may be provided. In particular, when the present invention is adopted to test an optical system to be tested other than an eye to be tested, the alignment validity judgement device 51, the plus/minus judgment device 52 and the alignment fluctuation judgement device 54 are not required, since the alignment of the apparatus according to the present invention relative to the optical system to be tested is stable, as long as it can be assumed that no visual acuity adjustment occurs at the optical system to be tested.

In the embodiment described above, when a defective value is obtained through measurement, the measuring operation is sustained without changing the judgement conditions or moving the fixation target 22 until the number of defective value measurements reaches the first specific value T1, and when it reaches the specific value T2, the measurement conditions are relaxed by extending the reference value for the measurement time. However, step S35 may be omitted, and instead, the condition relaxation and the fixation target movement implemented in step S21 may be repeated each time a measured value is determined to be a defective value until the number of defective measurements reaches T1. Alternatively, both steps S35 and S21 may be omitted.

The condition relaxation implemented by the condition relaxation device 70 is not limited to the extension of the measurement time described above. The condition relaxation device 70 may relax all of the validity conditions or some arbitrary selected validity conditions, in the judgement performed at the individual judgement devices of the validity condition judgment device 50. It is to be noted that judgement may be performed again using the relaxed conditions on measured values that have been stored as defective values to restore them as valid values. The condition relaxation described above may be implemented gradually using specific values that are set in advance as the time that is being counted by the measurement time judgement device 64 elapses. The following is an explanation of an example of such condition relaxation.

If the standard deviation of the measured values obtained within a measurement time of 0~ less than 2 seconds is equal to or less than 0.25 diopters, the measuring operation is terminated, whereas if it is larger than 0.25 diopters, the measuring operation continues, since the measured values have not yet stabilized. Likewise, if the standard deviation of measured values obtained between 2 seconds or more and less than 4 seconds is equal to or less than 0.50 diopters, the measuring operation is terminated, whereas if it is larger than 0.50 diopters, the measuring operation continues, since the measured values have not yet stabilized. If the standard deviation of measured values obtained between four seconds or more and less than 6 seconds is equal to or less than 1 diopter, the measuring operation is terminated, whereas if it is larger than 1 diopter, the measuring operation continues since the measured values have not yet stabilized. Then, the measuring operation is terminated unconditionally when 6 seconds have elapsed.

The following advantage is achieved by implementing judgement with the conditions changed by the measurement time judgement device 64. Namely, since there are states that are unique to a given eye E to be tested, and measurements may demonstrate inconsistency due to unstable reflected light from the eye ground if turbidity, scarring or the like is present in a transparent portion of the eye. In such a case, measured values will be inconsistent no matter how long the measuring operation is continued, and thus, an unnecessarily large burden is placed on the subject through an excessively long measuring operation. In order to avoid this, by gradually relaxing the conditions, if the termination conditions are not satisfied after a measuring operation has been performed over a specific length of time, the measuring operation can be carried out smoothly while minimizing the burden placed upon the subject.

Since the automatic measurement mode, in which a measuring operation is started based upon the alignment judgement and the measuring operation is automatically terminated and the manual measurement mode, in which the operator himself makes a judgement in regard to the alignment to start a measuring operation and is terminated the measuring operation based upon his own judgement are available in the embodiment explained above, the operator can select either of the modes to suit the particular eye to be tested.

Having the two modes that can be selected achieves the following advantage. Namely, since there are conditions that are unique to a given eye to be tested, the measurements may be inconsistent due to unstable reflected light from the eye ground if turbidity, scarring or the like is present at a transparent portion of the eye. In such a case, since the measured values are inconsistent, a greater length of measurement time is required in the automatic measurement mode compared to that required by normal subjects, resulting in an increased burden placed upon the subject. In order to avoid this, the apparatus according to the present invention, which can be switched to the manual measurement mode, is switched to the manual measurement mode before the measuring operation when testing a subject who is known to have a problem in advance. With this, a measuring operation can be carried out while placing a minimum necessary burden on the subject. Since the decision-making in regard to the measurement time is implemented in step S17 in the defective measurement processing loop, the measuring operation is terminated when a specific length of time has elapsed before the number of defective measurements reaches a specific value so that the measuring operation does not become extended undesirably and so that the burden placed upon the subject can be reduced.

Second Embodiment

Figure 5A:
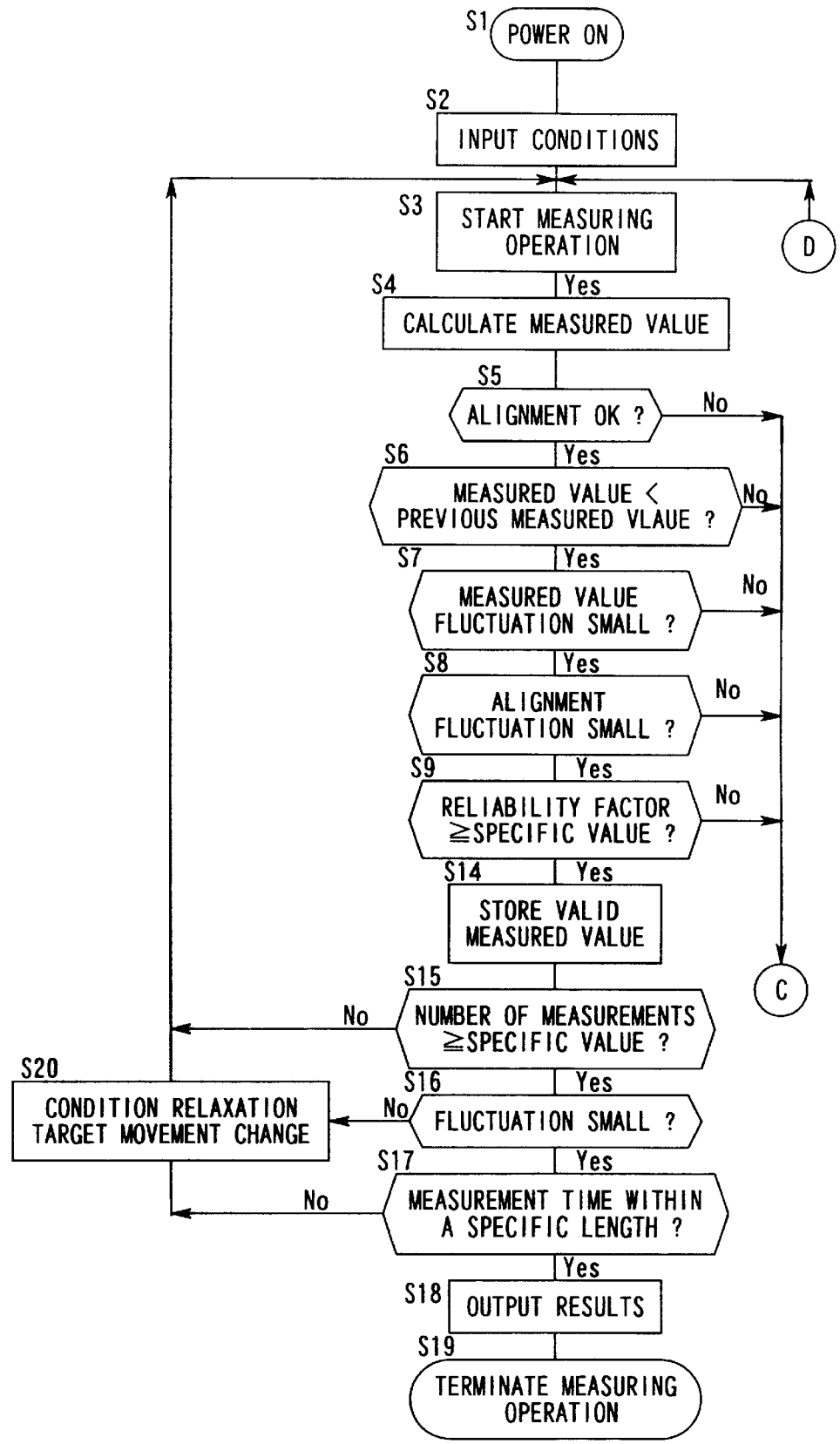
FIGS. 5A and 5B are flowcharts illustrating a measuring operation performed by the subjective eye refractive power measuring apparatus in a second embodiment.
Figure 5B:
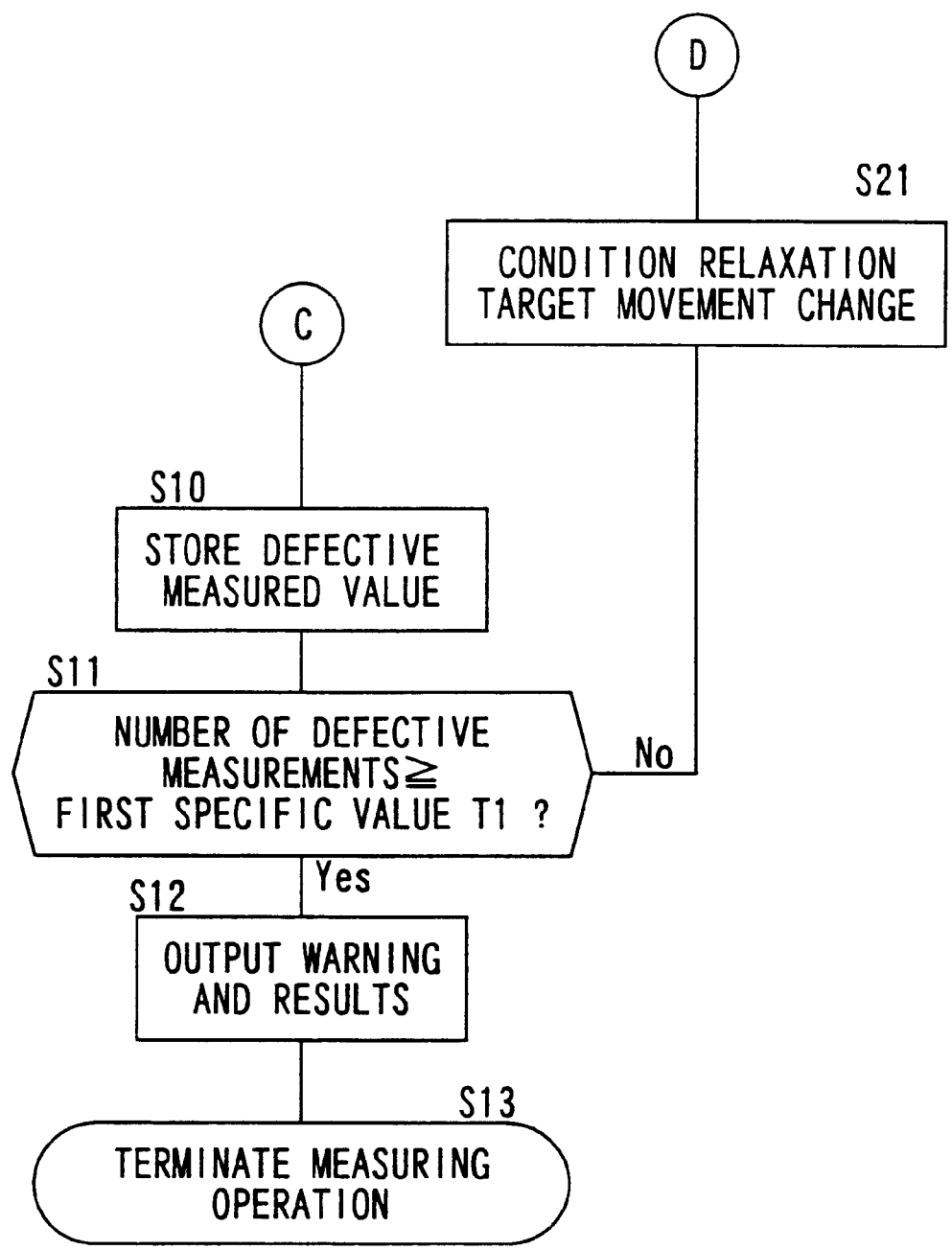

The second embodiment of the present invention is now explained in reference to FIGS. 5A and 5B. The explanation will mainly focus on differences, with the same reference numbers assigned to steps similar to those in FIGS. 4A and 4B. In the second embodiment, the judgement in regard to the measurement time implemented in step S17 is carried out after a specific number of valid measured values have been obtained. In addition, the judgement in step S35 as to whether or not the number of defective measurements has reached the second specific value T2 is omitted. Consequently, the condition relaxation and the fixation target movement are implemented each time a measured value is judged to be defective until the number of defective measurements is judged to be equal to or greater than the first specific value in step S11. In the second embodiment implemented in this manner, too, automatic measurement is achieved as in the first embodiment. It is to be noted that FIGS. 5A and 5B illustrate the operation executed in the automatic measurement mode.

Third Embodiment

Figure 6:
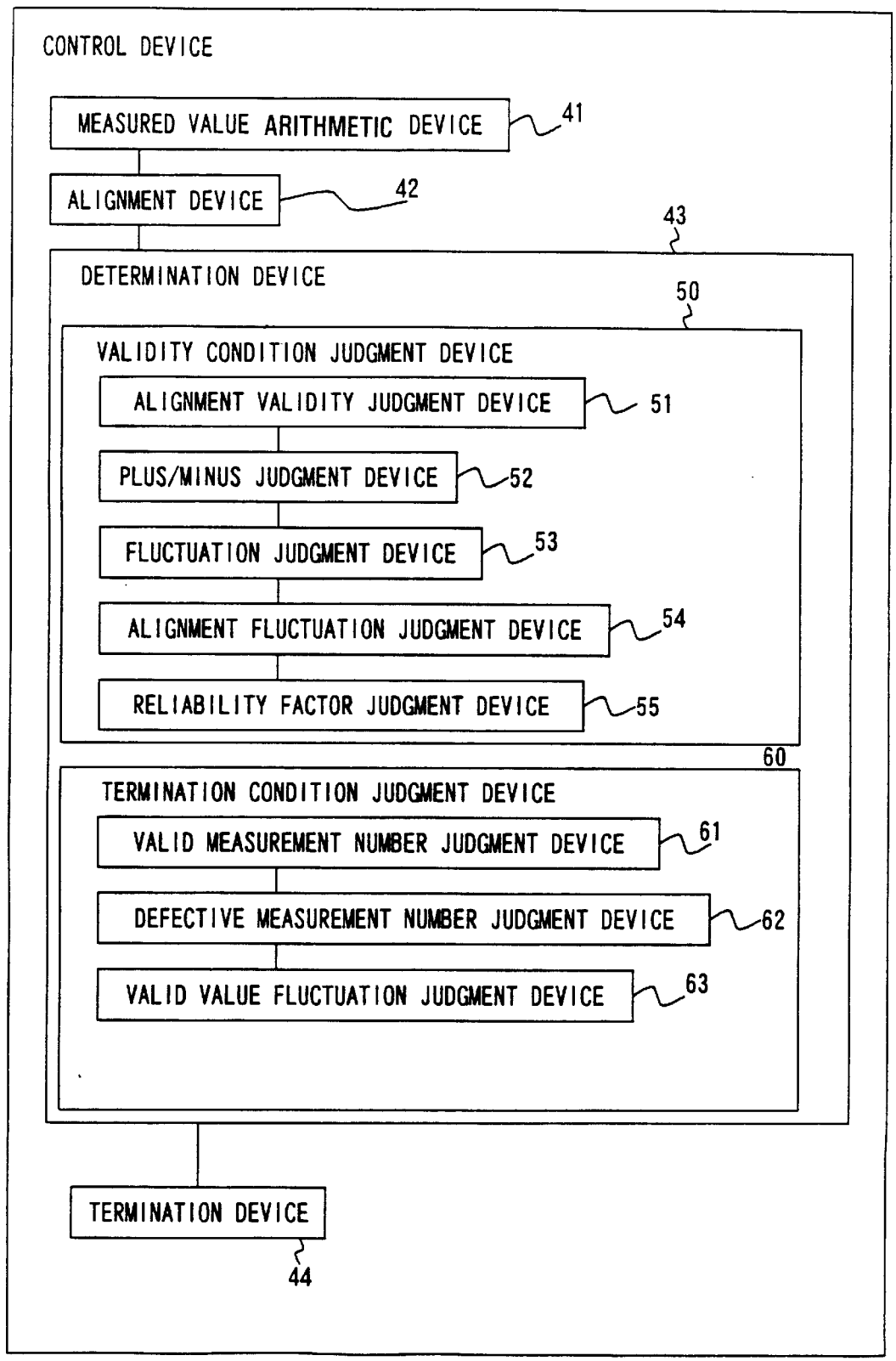
FIG. 6 is a functional block diagram of the control device in the subjective eye refractive power measuring apparatus in a third embodiment.
Figure 7:
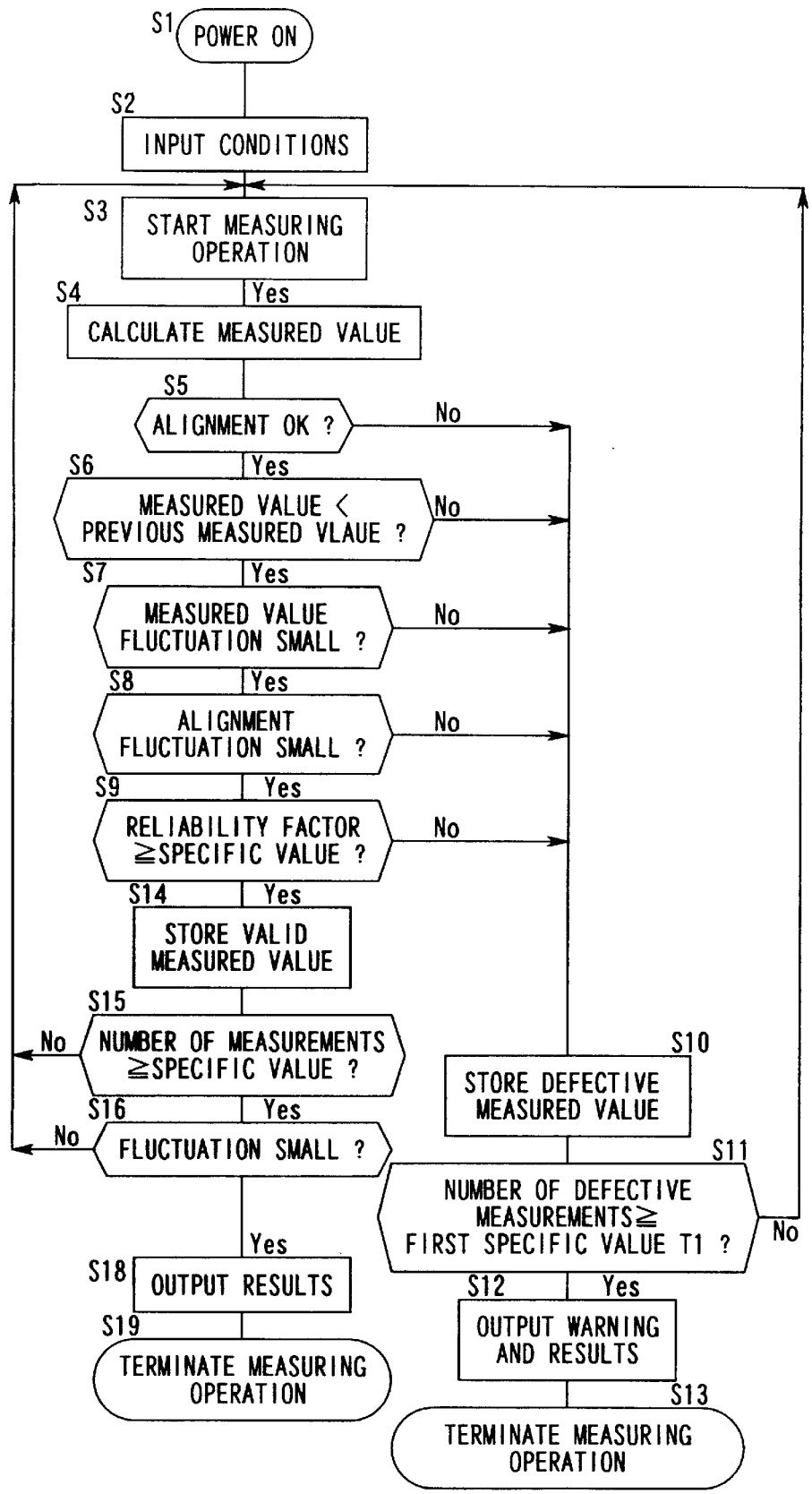
FIG. 7 is a flowchart illustrating a measuring operation performed by the subjective eye refractive power measuring apparatus in the third embodiment.
Figure 8:
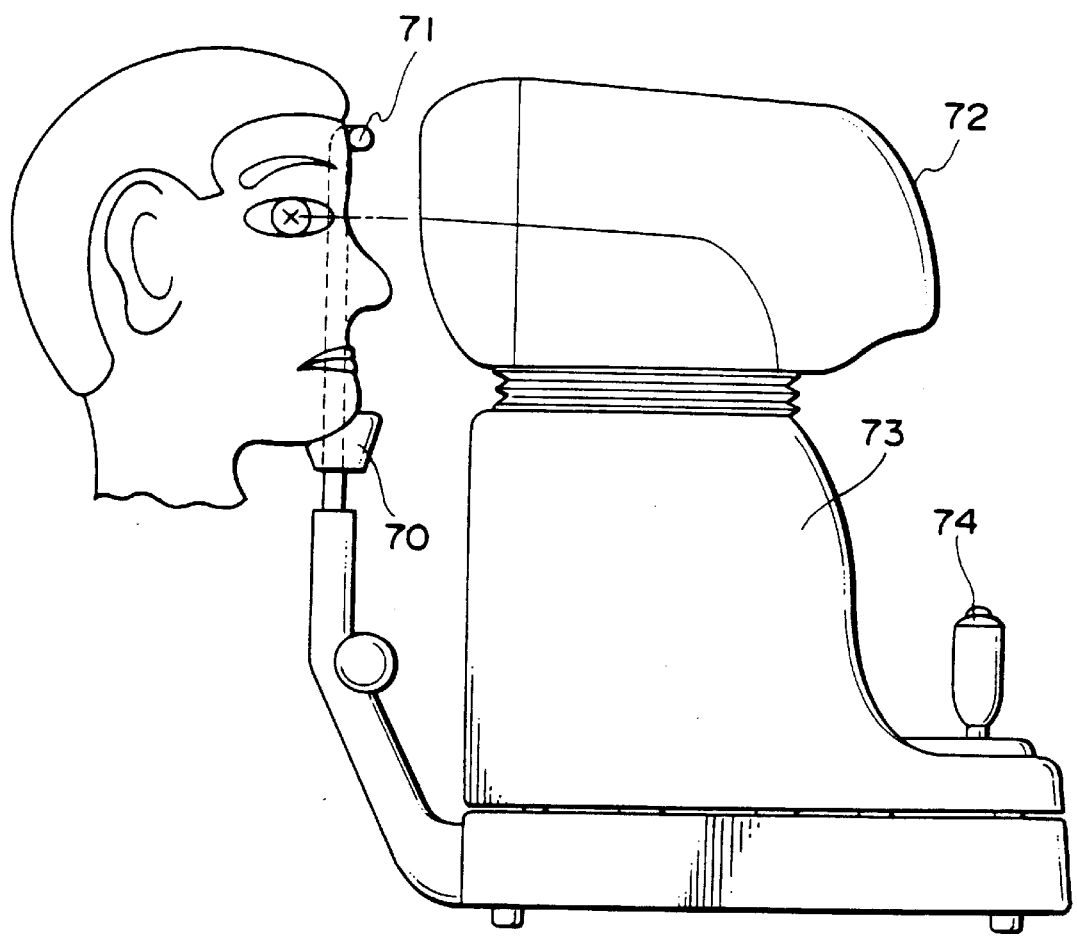
FIG. 8 is a side elevation of a stationary subjective eye refractive power measuring apparatus in the prior art in an operating state.
Figure 9:
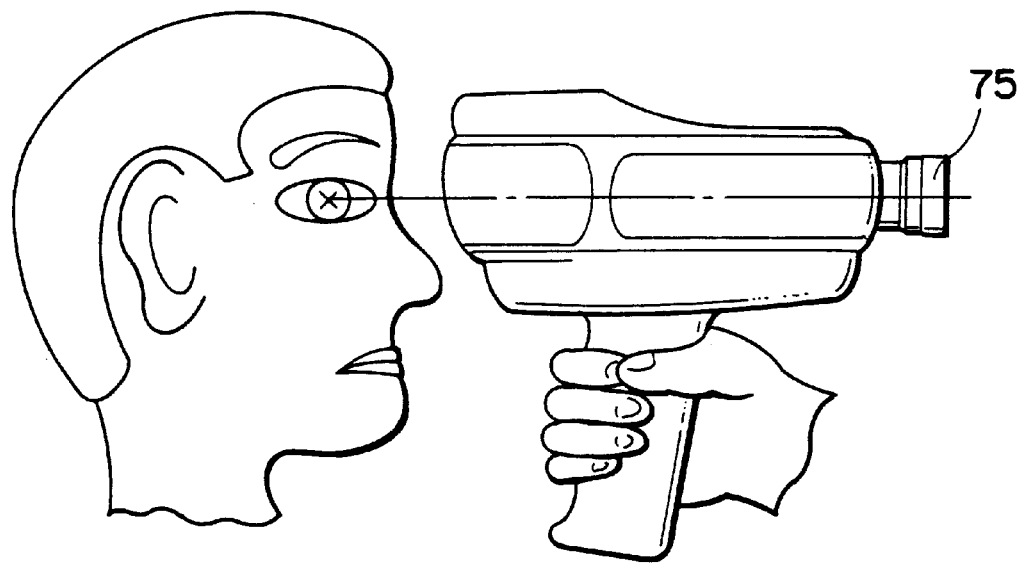
FIG. 9 is a side elevation of a hand-held subjective eye refractive power measuring apparatus in the prior art in an operating state.

Now, an explanation is given on the third embodiment in reference to FIGS. 6 and 7. The explanation will mainly focused on differences with the same reference numbers assigned to components and steps similar to those in FIGS. 3, 4A and 4B. In the third embodiment, the measurement time judgement device 64, the condition relaxation device 70 and the fixation target moving device 80 are omitted, the judgement in regard to the measurement time implemented in step S17, the determination as to whether or not the number of defective measurements has reached the second specific value T2 implemented in step S31 and the condition relaxation and the fixation target movement implemented in steps S20 and S21 are omitted. Thus, the measuring operation continues with the same measurement conditions each time a measured value is judged to be defective until the number of defective measurements is judged to be equal to or greater than the first specific value in step S11. In the third embodiment implemented in this manner, too, automatic measurement is achieved as in the first embodiment. It is to be noted that FIGS. 6 and 7 illustrate the operation executed in the automatic measurement mode.

It should be noted that a subjective eye refractive power measuring apparatus according to the present invention may include a controller comprising discrete circuits instead of a computer system as shown in FIG. 3.

What is claimed is:

1. A subjective eye refractive power measuring apparatus for objectively measuring optical performance of an optical system to be tested comprising:

a measuring optical system including a measuring element that outputs a detection signal corresponding to the refractive power of the optical system to be tested;

an arithmetic calculator that calculates a measured value related to the optical performance based upon an output signal from said measuring element;

a determination device that determines whether or not specific conditions in regard to termination of a measuring operation are satisfied based upon at least either a measured value obtained at said arithmetic calculator or a length of measurement time required for a measuring operation; and a termination device that implements specific control in order to terminate a measuring operation when said determination device determines that said specific conditions are satisfied.

2. A subjective eye refractive power measuring apparatus according to claim 1, wherein:

said determination device includes;

a validity condition judgment portion that judges whether or not a measured value calculated at said arithmetic calculator satisfies specific validity conditions for recognizing said measured value as a valid value; and a termination condition judgment portion that judges whether or not specific termination conditions for terminating a measuring operation are satisfied based upon, at least, either a measured value judged to be valid by said validity condition judgment portion or a measured value judged to be not valid by said validity condition judgment portion.

3. A subjective eye refractive power measuring apparatus according to claim 2, further comprising:

an alignment measurement device that outputs a signal corresponding to an alignment state of said measuring optical system relative to the optical system to be tested, wherein:

said validity condition judgment portion includes at least one of;

an alignment validity judgment portion that judges whether or not said alignment state of said measuring optical system relative to the optical system to be tested is correct based upon an output signal from said alignment measurement device, when obtaining a measured value at said arithmetic calculator;

a plus/minus judgment portion that judges whether or not a measured value obtained at said arithmetic calculator is negative relative to a measured value obtained immediately before said measured value is obtained;

a fluctuation judgment portion that judges whether or not a measured value obtained at said arithmetic calculator is within a specific range relative to a reference value calculated based upon measured values obtained before said measured value is obtained;

an alignment fluctuation judgment portion that, when a measured value is obtained at said arithmetic calculator, judges whether or not a change in said alignment state occurring between before said measured value is obtained and after said measured value is obtained, is within a specific range based upon said output signal from said alignment measurement device; and a reliability factor judgment portion that judges whether or not a reliability factor calculated based upon said measured value obtained at said arithmetic calculator is within a specific range; and said validity condition judgment portion judges that said validity conditions are satisfied when results of judgments made by all judgment portions constituting said validity condition judgment portion satisfy corresponding conditions.

4. A subjective eye refractive power measuring apparatus according to claim 2, wherein:

said termination condition judgment portion includes at least one of:

a valid measurement number judgment portion that judges whether or not a number of measurements judged to be valid by said validity condition judgment portion has reached a specific value;

a valid value fluctuation judgment portion that judges whether or not a measured value judged to be valid by said validity condition judgment portion is equal to or greater than specific factor; and a time judgment portion that judges whether or not a measured value judged to be valid by said validity condition judgment portion has been obtained within a specific length of measurement time; and said termination condition judgment portion judges that said termination conditions are satisfied when results of judgments made by all judgment portions constituting said termination condition judgment portion satisfy corresponding conditions.

5. A subjective eye refractive power measuring apparatus according to claim 4, further comprising:

a condition relaxation device that relaxes conditions used by at least one of said judgment portions to perform a valid/defective judgement on, at least, one occasion, when said valid value fluctuation judgment portion has judged that the measured value judged to be valid is not within said specific range and when said time judgment portion has judged that a measuring operation could not be terminated within said specific length of measurement time.

6. A subjective eye refractive power measuring apparatus according to claim 5, wherein:

said condition relaxation device expands said specific range set for said valid value fluctuation judgment portion and/or extends said specific length of measurement time set for said time judgment portion.

7. A subjective eye refractive power measuring apparatus according to claim 2, wherein:

said termination condition judgment portion includes at least either;

a defective measurement number judgment portion that judges whether or not a number of defective measurements judged to be not valid by said validity condition judgment portion has reached a specific value; or a time judgment portion that judges whether or not a measuring operation could not be terminated within said specific length of measurement time; and said termination condition judgment portion makes a judgment on said termination conditions based upon results of a judgment made by either one of said judgment portions.

8. A subjective eye refractive power measuring apparatus according to claim 7, further comprising:

a storage device for storing measured values obtained at said arithmetic calculator, that stores measured values judged to be not valid by said validity condition judgment portion as defective values, wherein:

said termination device outputs defective values stored in said storage device and terminates a measuring operation, at least either when said defective measurement number judgment portion has judged that the number of defective measurements has reached said specific value or when said time judgment portion has judged that a measuring operation could not be terminated within said specific length of measurement time.

9. A subjective eye refractive power measuring apparatus according to claim 7, wherein:

said termination device outputs a warning and terminates a measuring operation either when said defective measurement number judgment portion has judged that the number of defective measurements has reached said specific value or when said time judgment portion has judged that said measuring operation could not be terminated within said specific length of measurement time.

10. A subjective eye refractive power measuring apparatus according to claim 7, further comprising:

a condition relaxation device that relaxes conditions used by at least one of said judgment portions to perform a valid/defective judgement on, at least, one occasion when said defective number measurement judgment portion has judged that the number of defective measurements has reached said specific value and when said time judgment portion has judged that a measuring operation could not be terminated within said specific length of measurement time.

11. A subjective eye refractive power measuring apparatus according to claim 10, wherein:

said condition relaxation device increases said specific value set for said defective measurement number judgment portion and/or extends said specific length of measurement time set for said time judgment portion.

12. A subjective eye refractive power measuring apparatus according to claim 1, further comprising:

a condition setting device that freely sets specific conditions related to termination of a measuring operation.

13. A subjective eye refractive power measuring apparatus according to claim 1, further comprising:

a fixation target indicator device that indicates a fixation target to a subject, wherein:

a fixation target movement is changed by said fixation target indicator device when said termination condition judgment portion has judged that said specific conditions related to termination of the measuring operation are not satisfied.

14. A subjective eye refractive power measuring apparatus for objectively measuring optical performance of an optical system to be tested, comprising:

a measuring element that outputs a signal corresponding to the optical performance of said optical system to be tested;

an arithmetic device that calculates a measured value related to the optical performance based upon an output signal from said measuring element; and a mode switching device that switches between a manual measurement mode in which a measuring operation is started and terminated based upon judgment of a operator and an automatic measurement mode wherein judgments in regard to a measuring operation start and a measuring operation termination are automatically made.

* * * * *